US008865399B2

(12) United States Patent
Schofield et al.

(10) Patent No.: US 8,865,399 B2
(45) Date of Patent: Oct. 21, 2014

(54) **PHAGE-MEDIATED BIOLUMINESCENT DETECTION OF *YERSINIA PESTIS***

(75) Inventors: David A. Schofield, Hollywood, SC (US); Ian J. Molineux, Austin, TX (US)

(73) Assignee: Guild Associates, Inc., Dublin, OH (US)

( * ) Notice: Subject to any disclaimer, the term of this patent is extended or adjusted under 35 U.S.C. 154(b) by 637 days.

(21) Appl. No.: 12/992,488

(22) PCT Filed: May 13, 2009

(86) PCT No.: PCT/US2009/043776
§ 371 (c)(1),
(2), (4) Date: Nov. 12, 2010

(87) PCT Pub. No.: WO2009/140375
PCT Pub. Date: Nov. 19, 2009

(65) Prior Publication Data

US 2011/0076672 A1 Mar. 31, 2011

Related U.S. Application Data

(60) Provisional application No. 61/127,506, filed on May 14, 2008.

(51) Int. Cl.
*C12Q 1/70* (2006.01)
*C12N 7/01* (2006.01)
*C12Q 1/68* (2006.01)
*C12Q 1/04* (2006.01)

(52) U.S. Cl.
CPC ................ *C12Q 1/04* (2013.01); *C12Q 1/6888* (2013.01); *G01N 2333/24* (2013.01)
USPC .......................... 435/5; 435/252.3; 435/320.1

(58) Field of Classification Search
CPC .................................... C12Q 1/70; C12N 7/01
See application file for complete search history.

(56) References Cited

U.S. PATENT DOCUMENTS

| | | | | |
|---|---|---|---|---|
| 4,861,709 A | 8/1989 | Ulitzur et al. | ..................... | 435/6 |
| 2007/0072174 A1 * | 3/2007 | Sayler et al. | ...................... | 435/5 |

FOREIGN PATENT DOCUMENTS

| | | |
|---|---|---|
| WO | WO 99/45354 | 9/1999 |
| WO | WO 03/035889 | 5/2003 |

OTHER PUBLICATIONS

Garcia et al. (Virology, Mar. 1, 2008, vol. 372, p. p. 85-96).*
Loessner et al. (Applied and Envirnmental Microbiology, 1996, p. 113-1140).*
Abremski, et al., 1986, *J Biol Chem* 261:391-6, 1986.
Bossi, et al., 2006, *Cell Mol Life Sci* 63:2196-212, 2006.
Choi, K. H., et al., 2008, *Appl Environ Microbiol* 74:1064-75, 2008.
Conchas, R. F., et al., 1990, *Gene* 87:133-7, 1990.
D'Aoust, J. Y., et al., 1988, *J Dairy Sci* 71:3230-6, 1988.
Dennis, D. T., et al., 1999, *Plague Manual: Epidemiology, Distribution, Surveillance, and Control*, 1999.
Escher, A., et al., 1989, *Proc Natl Acad Sci U S A*, 86:6528-32, 1989.
Garcia, E., et al., 2003, *J Bacteriol*, 185:5248-62, 2003.
Garcia, E., et al., 2008, *Virology*, 372:85-96, 2008.
Lin, L. Y., et al., 2004, *Biochemistry*, 43:3183-94, 2004.
Liu, Q., et al., 1993, *Proc Natl Acad Sci U S A*, 90:1761-5, 1993.
Loessner, M. J., et al., 1996, *Appl Environ Microbiol.*, 62:1133-40, 1996.
Mackey, B. M. et al., 1994, *J Appl Bacteriol.*, 77:149-54, 1994.
Meyer, K. F. 1974, *Plague immunization. Journal of Infectious Diseases* 129:S13-S18, 1974.
Sambrook, J., et al., 1989, *Cold Spring Harbor Press, New York*, 1989.
Schofield, D. A., et al., 2001, *J Bacteriol.*, 183:6947-50, 2001.
Schofield, D. A., et al., 2002, *Curr Microbiol.*, 44:425-30, 2002.
Schofield, D. A., et al., 2002, *FEMS Microbiol Lett.*, 215:237-42, 2002.
Schofield, D. A., et al., 2003, *Appl Environ Microbiol.*, 69:3385-92, 2003.
Sternberg, N., et al., 1981, *J Mol Biol.*, 150:467-86, 1981.
Studier, F. W. 1981. *J Mol Biol.*, 153:493-502, 1981.
Wright, J. J., et al., 1992, *Embo J* 11:1957-64, 1992.
Young, R. 1992, *Microbiol Rev.*, 56:430-81, 1992.
Zierdt, C. H. 1988, *Appl Environ Microbiol.*, 54:2590, 1988.
Mole, R.J. et al., 2001, Chem Technol Biotechnol, 76: 683-688, 2001.
Gunnison, J.B., et al., 1951, The Journal of Infectious Disease, 88, 3, 254-255, 1951.
Cavanaugh, D.C., et al., 1953, American Journal of Clinical Pathology, 23, 6, 619-620, 1953.
International Search report and Written Opinion; PCT/US2009/043776; pp. 15, Dec. 1, 2009.
Schofield et al.; "Rapid identification and antibiotic susceptibility testing of *Yersinia pestis* using bioluminescent reporter phage"; Journal of Microbiological Methods; vol. 90; pp. 80-82, 2012.
Schofield et al.; "Diagnostic Bioluminescent Phage for Detection of *Yersinia pestis*"; Journal of Clinical Microbiology; vol. 47, No, 12; pp. 3887-3894, Dec. 2009.
European Office Action; Application No. 09 747 459.7-2402; pp. 5, Sep. 18, 2012.
International Preliminary Report on Patentability; PCT/US2009/043776; pp. 7, Nov. 25, 2010.

* cited by examiner

*Primary Examiner* — Agnieszka Boesen
(74) *Attorney, Agent, or Firm* — Baker Botts L.L.P.

(57) ABSTRACT

The present disclosure relates to compositions, methods, systems and kits for the detection of microorganisms of the *Yersinia* species including *Yersinia pestis*. The disclosure relates to recombinant phage operable to infect a *Yersinia* microorganism, the phage comprising a detectable reporter. Detection systems of the disclosure may comprise a phage operable to infect a *Yersinia* microorganism, and may comprise a reporter nucleic acid expressible upon infection of a *Yersinia* microorganism by the phage. The system may be operable to detect the expression of the reporter. A detectable reporter may comprise any gene having bioluminescent, colorimetric and/or visual detectability. For example, a detectable reporter may comprise one or more luxAB genes detectable by emission, enhancement and/or change in spectrum of bioluminescent light. Live and infectious *Yersinia* microbes may be detected by the compositions, methods, systems and kits described herein.

11 Claims, 4 Drawing Sheets

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
taaggaggta aaaaaatg                                                        18

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```

```
ttgaca                                                                      6

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 tataat                                                                      6

<210> SEQ ID NO 4
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 aaaaa                                                                       5

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(9)
<223> OTHER INFORMATION: a, c, t, g, unknown or other
<220> FEATURE:
<221> NAME/KEY: modified_base
<222> LOCATION: (16)..(32)
<223> OTHER INFORMATION: a, c, t, g, unknown or other

<400> SEQUENCE: 5
aaaaannnnt tgacannnnn nnnnnnnnnn nntataat                                  38
```

US 8,865,399 B2

PHAGE-MEDIATED BIOLUMINESCENT DETECTION OF *YERSINIA PESTIS*

PRIORITY

This application is a 371 U.S. national application of International Application Number PCT/US2009/043776 filed May 13, 2009, which designates the United States, and claims priority to U.S. Provisional Application Ser. No. 61/127,506, filed May 14, 2008. The contents of which are hereby incorporated by reference in its entirety.

GOVERNMENT RIGHTS

This invention was made with government support under government contract number 1R43AI082698-01, Plague related NIH SBIR Grant. The U.S. Government has certain rights in this invention.

FIELD OF THE DISCLOSURE

The present disclosure relates to compositions, methods, systems and kits for detection of microbes. In some embodiments, the compositions, methods, systems and kits of the disclosure are directed to the detection and/or identification of biological pathogens of *Yersinia* species (e.g., *Yersinia pestis*).

BACKGROUND OF THE DISCLOSURE

*Yersinia pestis* is classified by the Centers for Disease Control and Prevention (CDC) and the National Institutes of Health (NIH) as a Category A priority bacterial pathogen that will most likely be used in a bioterrorist attack. *Y. pestis* is the etiological agent of the plague (Black Death), a transmissible disease that has been responsible for millions of deaths throughout the course of history. Typically, humans contract plague after being bitten by a rodent flea that carries the plague bacterium or by handling an infected animal. Millions of people in Europe died from plague during the Middle Ages, when human homes and places of work were inhabited by flea-infested rats.

Although the natural occurrence of the disease is now relatively rare, the deliberate release of *Y. pestis* is a real threat. Dispersal will most likely be in the form of an aerosolized release over a populated area. The first signs of an attack will be outbreaks of pneumonic plague 1-4 days later. If left untreated, pneumonic plague is nearly always fatal. *Y. pestis* may be transmitted from person to person. Transmission may occur through infectious respiratory droplets from pneumonic cases of the plague, or even from inhalation from contaminated clothes.

The use of *Y. pestis* as a biological weapon is not without precedent. The Tartars, during the siege of the Genoese-controlled Black Sea port of Kaffa, hurled plague-infected corpses over the city walls into the huddled city. During World War II, the Japanese reportedly released plague-infected fleas over populated areas of China, which resulted in sporadic plague outbreaks. Recent technological advances have enabled *Y. pestis* to be directly aerosolized, which is considered to be the most likely way the agent would be dispersed. The World Health Organization (WHO) estimates that an aerosolized release of 50 kg over a populated city could cause 150,000 cases of pneumonic plague and 36,000 fatalities. Compounding this threat is the possibility of deliberately releasing engineered antibiotic resistant strains which were reportedly produced in the former Soviet Union. Consequently, the potential for public disruption and panic would be severe.

SUMMARY

Accordingly, a need has arisen for compositions, methods, systems, and/or kits for easily and/or rapidly detecting microbes (e.g., *Yersinia pestis*) in a laboratory and/or in a non-laboratory setting.

The present disclosure relates, according to some embodiments, to compositions, methods, systems, and/or kits for easy and/or rapid detection of microbes (e.g., of the *Yersinia* sp.) in a laboratory and/or in a non-laboratory setting.

In some embodiments, the present disclosure relates to a phage operable to infect a *Yersinia* microorganism comprising a reporter. In some embodiments, the reporter may comprise a nucleic acid. The nucleic acid may encode one or more detectable gene products. For example, the reporter may comprise a nucleic acid that, upon expression, leads to the production of one or more detectable products. Detectable gene products may include, for example, enzymes that catalyze bioluminescent reactions (e.g., encoded by luxAB) and/or fluorescent proteins (e.g., GFP, DsRed) that may be detected with a light detector. Detectable gene products may include, for example, enzymes that catalyze reactions with colored reactants and/or products (e.g., encoded by lacZ and/or gusA) that may be detected colorimetrically.

The disclosure relates to phage that may infect a *Yersinia* microorganism. In some embodiments, the disclosure relates to a phage of serovar 1, and/or serovar 2, and/or serovar 3, and/or serovar 4, or of any serovar that *Yersinia*-specific phages may be categorized into. In some embodiments, the phage may be a lytic phage, such as a φA1122 phage. In some embodiments, the phage may be a temperate phage and may comprise a L-413C phage.

The present disclosure also relates to a detection system comprising: (a) a phage operable to infect a *Yersinia* microorganism, comprising a reporter configured and arranged to be expressed upon infection of the *Yersinia* microorganism by the phage; and (b) a detector operable to detect reporter expression.

Expression of a gene, in some embodiments, may include transcription and/or translation. According to some embodiments, expression may include post transcriptional and/or posttranslational modification(s) of a gene product. In some embodiments, one may detect a detectable gene product that may be formed following phage binding and/or infection of a *Yersinia* microorganism. For example, a detectable gene product may include a product of transcription (e.g., an RNA), a product of translation (e.g. a peptide or a protein), and/or a product of post transcriptional and/or posttranslational modification. A detectable gene product, in some embodiments, may include a product that may form as a result of phage binding or infection which does not require transcription and/or translation.

In some embodiments, a reporter may comprise a nucleic acid. A reporter nucleic acid, in some embodiments, may be operably linked to one or more *Yersinia* expression control elements that control the expression of one or more detectable genes. Expression of a detectable gene may refer to transcription, and/or synthesis of RNA and/or stable accumulation of RNA (e.g., mRNA). Expression may also refer to translation of mRNA into a polypeptide as well as modification of such a polypeptide or protein by posttranslational mechanisms. For example, a *Yersinia* expression control element may comprise one or more transcriptional control elements (non-limiting examples include promoters (e.g., −10 box, −35 box, heat-shock promoters, etc.), enhancers, inducers, transcriptional repressors, transcriptional terminators, RNA processing or stabilizing elements, one or more translational control elements (non-limiting examples include translation leader sequences, RNA processing site, effector binding site and stem-loop structure), one or more posttranslational modifying elements, and/or combinations thereof.

In some embodiments of the disclosure, a reporter nucleic acid may comprise one or more luxAB gene(s). LuxAB genes encode for an enzyme, a luciferase, that catalyzes the production of bioluminescent light that may be detected using a photodetector. Nucleic acids encoding luxAB genes may be derived from any organism of any species. For example, a luxAB from *Vibrio harveyi, Xenorhadbus luminescens, V. fischeri, Photinus pyralis* (firefly), *Photobacterium* sp., *Photorhabdus luminescens*, or any species expressing luxAB may be used. In some embodiments, one or more luxAB genes encoding mutations that emit light at various (different) wavelengths may be used.

A nucleic acid construct, also referred to as a vector or a cassette, comprising a luxAB gene (or any other detectable gene) may have expression control elements, such as but not limited to the following: transcriptional control elements (for example, promoter elements such as but not limited to those described above; enhancers; inducers; transcriptional repressors; and/or transcriptional terminators, etc.); translational control elements; posttranslational modifying elements; and/or combinations thereof that may control its expression. In some embodiments, one or more of the expression control elements may be derived from *Yersinia* sp. In some embodiments, one or more of the expression control elements may require at least one regulatory moiety derived from a *Yersinia* organism for turning on the expression of the luxAB gene (or any other detectable gene). An exemplary regulatory moiety derived from a *Yersinia* organism may be a protein (e.g., a trans-activating protein), a gene regulatory element (such as a ribosome), an RNA, a DNA, a co-factor. In some embodiments, a nucleic acid construct having a luxAB gene (or any other detectable gene) may be detectable once transformed or transfected into a *Yersinia* cell or in a live *Yersinia* cell.

In some embodiments, one or more promoters used to control the expression of a detectable gene (such as luxAB, or a fluorescent protein gene) may be derived in their entirety from a native gene (such as from a *Yersinia* Sp.), or be composed of different elements derived from different promoters (from *Yersinia* sp. or those found in nature), or may even comprise synthetic DNA segments. The location of a detectable gene (i.e., such as but not limited to a luxAB gene, a fluorescent protein gene) in a nucleic acid construct, in accordance with the teachings of the present disclosure, may vary based on expression characteristics which may depend on the particular nucleic acid construct and/or expression control sequences employed. One of skill in the art will realize that such variations are all within the scope of the present disclosure.

In some embodiments, a reporter may comprise a nucleic acid encoding the luxCDE genes (from any species) in addition to a luxAB gene. LuxCDE genes encode a fatty acid reductase complex that synthesizes fatty aldehydes which are substrates for the luminescence reaction. This may partially and/or completely eliminate the need to add aldehyde substrates to produce and/or detect bioluminescence.

A detection system of the disclosure may be configured to detect any *Yersinia* microorganism. In some embodiments, *Yersinia pestis* may be detected. In some embodiments, other human pathogenic *Yersinia* microorganisms, for example, *Yersinia enterocolitica, Yersinia pseudotuberculosis*, and combinations thereof may be detected. The detection system of the disclosure may also detect *Yersinia* microorganisms that are pathogenic to other animals, birds, fish, and the like. For example, *Yersinia ruckeri* (a fish pathogen) may be detected.

In some embodiments, a detection system may include phage that may infect a *Yersinia* microorganism. According to some embodiments, any phage that infects any *Yersinia* microorganism may be used. A phage may include a phage of serovar 1, and/or serovar 2, and/or serovar 3, and/or serovar 4, or of any serovar or any other classification that *Yersinia*-specific phages may be categorized into, according to some embodiments. A detection system, in some embodiments, may include a lytic phage (e.g., a φA1122 phage). In some embodiments, a detection system may include a temperate phage (e.g., a L-413C phage).

The disclosure also relates to methods of detecting the presence of a *Yersinia* microorganism in a test sample. In some embodiments, a detection method may comprise: a) providing a phage operable to infect a *Yersinia* microorganism, wherein the phage comprises a reporter configured and arranged to be expressed upon infection of the *Yersinia* microorganism by the phage; b) contacting the test sample with the phage under conditions that permits the phage to infect the *Yersinia* microorganism and express the reporter; and c) detecting expression of the reporter, if any, wherein detecting the reporter indicates that the *Yersinia* microorganism is present in the test sample.

Methods of the disclosure may be configured to detect any *Yersinia* microorganism from a test sample that may be suspected of comprising *Yersinia*, according to some embodiments. For example, human pathogenic *Yersinia* microorganisms such as *Yersinia pestis, Yersinia enterocolitica, Yersinia pseudotuberculosis*, and combinations thereof may be detected. Methods of the disclosure may also detect *Yersinia* microorganisms that are pathogenic to other animals, birds, fish, etc., for example, *Yersinia ruckeri* (a fish pathogen) may be detected. Test samples may be biological test samples collected from a human or an animal or they may be non-biological samples. Biological samples may include any sample derived from the body of an animal or human that may be infected or is suspected of being infected. Non-biological samples may include a food sample, a water sample, an air sample, and the like may be tested for the presence of a *Yersinia* microorganism.

In some embodiments, detecting expression of a reporter may comprise detecting bioluminescence. Detecting bioluminescence may comprise providing a substrate intended to react with a luxAB gene product. One exemplary substrate may comprise an aldehyde such as n-decanal. In embodiments where a luxCDE gene may also be present in a reporter system (on the same or separate reporter), detecting bioluminescence may not require the provision of an aldehyde substrate and/or may require providing a smaller amount of an aldehyde substrate as compared to when a luxCDE gene may not be present in the reporter system.

The present disclosure also relates to kits for detecting the presence of a *Yersinia* microorganism. A kit, in some embodiments, may be used in a laboratory and/or outside of a laboratory setting. In some embodiments, a kit according to the disclosure may comprise a) a phage operable to infect a *Yersinia* microorganism, comprising a reporter configured and arranged to be expressed upon infection of the *Yersinia* microorganism by the phage, in a suitable container; and b) one or more containers to mix the phage with a test sample that may comprise the *Yersinia* microorganism. A kit, according to some embodiments, may comprise a detector substrate in a suitable container. In some embodiments, a kit may comprise a bioluminescence detector (e.g., a photon detector; a detector configured and arranged to detect different wavelengths of bioluminescent light).

In some embodiments, a kit may comprise one or more *Yersinia* specific phages. Any phage that infects any *Yersinia* microorganism may be used. In some embodiments a kit of the disclosure may comprise one or more *Yersinia* microorganism as a control.

BRIEF DESCRIPTION OF THE DRAWINGS

Some embodiments of the disclosure may be understood by referring, in part, to the present disclosure and the accompanying drawings, wherein.

DETAILED DESCRIPTION

Figure 1:
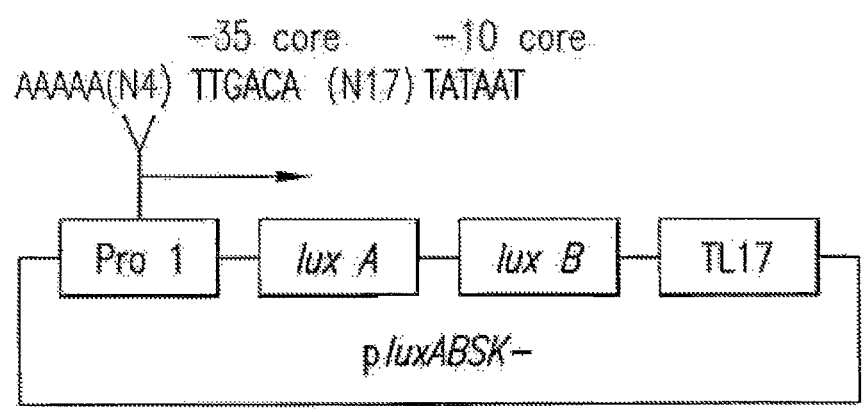
FIG. 1 illustrates a schematic of a luxAB expression cassette and Pro1 conserved nucleotides (arrow denotes direction of transcription), according to a specific example embodiment of the disclosure.

Current biological detection methods for the detection of *Yersinia pestis* may be time consuming and/or expensive and/or may require expensive laboratory equipment and/or expertise. Methodologies for rapid and sensitive *Y. pestis* detection are critically needed to combat the threat of deliberate release of this pathogen. Phage specific lysis assays, using *Y. pestis* specific phage, may be used as a diagnostic standard for the confirmed identification of *Y. pestis*. However, laboratory-based methods may require elaborate sample processing, and/or extensive incubation periods, and/or 18-24 hours to complete. Immunological methods using fluorescent-antibodies specific to *Y. pestis* F1 envelope glycoprotein and/or capsular antigen may be used. However, immunological methods may require long incubation and reaction periods, expensive reagents, and/or a laboratory setting to perform.

Rapid and sensitive detection methodologies may contribute to lower morbidity and save lives (e.g., where a bioterrorist attack affects a large population at once). Some embodiments of the present disclosure relate to compositions, methods, systems and kits for detection of microbes (e.g., *Y. pestis*), that may provide desirable speed and sensitivity and may be used in and/or outside of a laboratory.

The present disclosure relates, in some embodiments, to biological detection compositions, methods, systems and/or kits for rapid detection of a bacterial cell such as a *Yersinia* sp. cell. There are about 11 named species in the genus *Yersinia* of which three species are known to be human pathogens: *Yersinia pestis*, *Yersinia enterocolitica*, and *Yersinia pseudotuberculosis*. The compositions, methods, systems and/or kits of the present disclosure, in some embodiments, may be used, for the detection of one or more *Yersinia* species exemplified in non-limiting examples by the human pathogenic strains *Yersinia pestis, Yersinia enterocolitica, Yersinia pseudotuberculosis*, as well as mutations and genetically engineered variants thereof, etc. Without limiting any embodiment of the disclosure to a particular *Yersinia* organism, mechanism of action, symptom(s), and/or modes of disease transmission some *Yersinia*-mediated diseases and conditions are described.

*Y. pestis* is the etiologic agent of plague which is a zoonotic disease affecting rats and other rodents. *Y. pestis* may be transmitted from animal to animal by fleabites, which may also be the most common route of transmission to humans. *Y. pestis*-infected flea bites, leads to the migration of the bacterium to the lymph nodes and bubonic plague develops 2-8 days which is characterized by fever, chills, weakness and the development of swollen lymph nodes or buboes. In a minority of cases, the fleabites develop into septicemia without a bubo, or occasionally into pneumonic plague. The occurrence of the plague is rare in the U.S. with only an average of 5-15 cases reported each year, mostly in rural areas. The epidemiology of the disease, however, may be very different during deliberate release, because an aerosolized attack of *Y. pestis* would lead to a massive outbreak of pneumonic plague. Early detection and diagnosis would be desirable since the only indications of an attack would be outbreaks of illness 1-4 days later presenting as severe pneumonia. Pneumonic plague is nearly always fatal if untreated.

*Y. pseudotuberculosis* and *Y. enterocolitica* are enteropathogenic *Yersinia* strains that may be transmitted orally and cause a range of gastrointestinal diseases collectively referred to as yersiniosis. *Y. enterocolitica* generally infects young children and some associated symptoms include fever, abdominal pain, and diarrhea, which is often bloody. Symptoms typically develop 4 to 7 days after exposure and may last 1 to 3 weeks or longer. Symptoms in older children and adults include right-sided abdominal pain and fever which may be confused with appendicitis. In a small proportion of cases, complications such as skin rash, joint pain, or spread of bacteria to the bloodstream may occur. *Y. pseudotuberculosis* is the closest genetic relative to *Y. pestis* but may be distinguished from the plague bacteria by its clinical manifestations and by laboratory test results. *Y. pseudotuberculosis* related gastrointestinal diseases are relatively rare but human infections transmitted via contaminated water and foods have been reported.

Embodiments of the present disclosure provide for compositions, methods, systems and/or kits for detection of bacteria of any *Yersinia* sp. and may be useful in detecting the pathogenic strains of *Yersinia* that afflict humans and/or animals.

In some embodiments, the compositions, methods, systems and/or kits of the disclosure, comprise a bacteriophage that is operable to infect a *Yersinia* microorganism. In some embodiments, one or more bacteriophage specific to *Yersinia* (e.g., *Y. pestis*) may be used. *Y. pestis* specific phage may be placed into four serovars based on their immunogenicity: (i) serovar 1 consists of lytic phages and is exemplified by the plague diagnostic phage φA1122; (ii) serovar 2 is exemplified by the temperate phage L-413C; (iii) serovar 3 is exemplified by a temperate phage, termed P, and serovar 4 is exemplified by the phages Tal and 513. The lytic phages of serovar 1, and in particular, the 'plague diagnostic' phage φA1122, have a broad host strain infectivity and species specificity. These phages all have isometric hexagonal heads and short (13-42 nm) non-contractile tails. They belong to the family Podoviridae and are closely related to the *Escherichia coli* phages T3 and T7. The φA1122 genome has recently been sequenced and found to consist of 37,555 bp, encoding 51 predicted gene products, and a nucleotide identity of 89% to the *E. coli* phage T7 (GenBank Accession No. AY247822 and GenBank Accession Number NC_004777 as of 11-APR-2006). Phage φA1122 is 'specific' to *Y. pestis* species with the exception of the closely related species *Yersinia pseudotuberculosis*. However, temperature may be used to differentiate the two species since the phage does not grow on *Y. pseudotuberculosis* at 20° C. Moreover, the phage has a very broad host range within the species *Y. pestis*. According to the CDC, the ϕA1122 phage can grow and lyse on all but two of thousands of natural isolates of *Y. pestis* within the CDC collection. Consequently, due to its specific and broad strain infectivity, ϕA1122 is used by the CDC, the WHO, and the U.S. Army Medical Research Institute of Infectious Diseases as a diagnostic standard (lysis assay) for the confirmed identification of *Y. pestis*.

In some embodiments of the compositions, methods, systems and/or kits of the disclosure, the bacteriophage operable to infect a *Yersinia* microorganism may comprise a reporter. In some embodiments, the reporter is a detectable reporter. In some embodiments of the disclosure, a lytic phage, e.g., a ϕA1122 phage, may be used to detect *Yersinia* microorganisms. In some embodiments of the disclosure, a temperate phage, e.g., a L-413C phage, may be used to detect *Yersinia* microorganisms.

In some embodiments, a ϕA1122 phage may comprise a reporter. In some embodiments, a reporter may comprise a nucleic acid which leads to the production of a detectable gene product. In some embodiments, a detectable gene product may comprise a protein that is encoded by the luxAB genes from *Vibrio harveyi* (GenBank Accession No. E12410, version 1, last updated Apr. 20, 2006). In some embodiments, a phage may be a genetically engineered phage comprising nucleic acids encoding a detectable gene product, e.g., a luxAB gene that encodes a luciferase enzyme.

In some embodiments, a detectable gene product may comprise or consist of a luciferase enzyme. Contacting a luciferase enzyme with a suitable luciferin substrate may produce bioluminescence. Substrates for a luciferase enzyme may comprise an aldehyde (e.g., n-decanal). In some embodiments, detection of bioluminescence upon binding or infection of the bacterial cell by the phage detects the presence of the *Yersinia* microorganism. The bioluminescent light signal may be visualized by a simple hand-held photon-detection device and no processing of the sample may be required. In some embodiments, the light signal detected may be analyzed for different wavelengths. In some embodiments the detection of the detectable reporter gene product may be by PCR or immunological methods.

In some embodiments, the detection of bioluminescence may be achieved in a time of less than 30 minutes following infection with a recombinant phage of the disclosure. In some embodiments, the detection of bioluminescence, and hence of an *Yersinia* microbe, may be in a time less than 25 minutes, less than 20 minutes, less than 18 minutes, less than 17 minutes, less than 16 minutes, less than 15 minutes, less than 14 minutes, less than 13 minutes, less than 12 minutes, less than 11 minutes, less than 10 minutes, less than 9 minutes, less than 8 minutes, less than 7 minutes, less than 6 minutes, less than 5 minutes, less than 4 minutes less than 3 minutes, less than 2 minutes to less than 1 minute, following infection with a recombinant phage of the disclosure.

The lux genes control bioluminescence in a wide variety of species including marine and terrestrial species such as bacteria, dinoflagellates, fungi, fish, insects, shrimp, and squid. Cloning and expressing lux genes from different species have led to significant advances in understanding the molecular biology of bioluminescence. Lux operons may have a common gene organization of luxCDAB(F)E, with luxAB coding for the enzyme luciferase and luxCDE coding for the fatty acid reductase complex responsible for synthesizing fatty aldehydes which are substrates for the luminescence reaction. However, significant differences exist in their sequences and properties as well as in the presence of other lux genes (such as lux I, R, F, G, and H). In some embodiments, a luciferase-encoding nucleic acid (e.g., luxAB from any species) may also be used in the compositions, methods, systems and/or kits of the disclosure. For example, a luxAB from *Xenorhadbus luminescens* may be used. Other non-limiting examples include a luxAB from *V. fischeri, Photinus pyralis* (firefly), *Photobacterium* sp., and *Photorhabdus luminescens.*

In some embodiments, the phage operable to infect a *Yersinia* microorganism, may comprise in addition to a reporter, nucleic acids encoding for the luxCDE genes (from any species), which encode a fatty acid reductase complex that may synthesize fatty aldehydes which are substrates for the luminescence reaction. This may eliminate the need to add aldehyde substrates to detect bioluminescence.

Expression of recombinant ϕA1122 luxAB and light production may require a phage-infected bacterial cell being detected to have an active metabolism. In some embodiments, a phage reporter gene may be under the control of one or more transcriptional elements (such as but not limited to, promoters, enhancers, repressors, transcriptional terminators, etc.) and/or translational elements (such as but not limited to, ribosome binding sites). Posttranslational modifying elements may also be desirable. A reporter gene may comprise a nucleic acid encoding a detectable gene product as well as transcriptional and/or translational control elements for expression of the detectable gene product. Bacterial cellular machinery may be desirable for expression of a reporter gene comprising one or more bacterial transcriptional and/or translational elements. In some embodiments, production of the detectable gene product by the reporter nucleic acid may be dependent on one or more components of the bacterial cell that the phage is infecting. For example, expression of the reporter may indicate the presence of live and infectious bacteria as well as bacteria of a specific species. Since only viable cells produce a light signal, these example compositions, methods, systems and/or kits of the disclosure of the present disclosure detect viable and infectious bacterial cells. This is a distinct advantage over PCR detection methodologies and the immunological F1 antigen tests which detect the presence of *Y. pestis*, but yield no information as to whether the *Y. pestis* cells are viable and infectious.

In some embodiments, the present disclosure, relates to methods for preparing a bacteriophage configured and arranged to detect a microbe. For example, a *Y. pestis* luxAB reporter phage may be generated using the diagnostic plague phage ϕA1122. LuxAB may be cloned into an expression cassette under the transcriptional and translational control of preferred *Yersinia* expression sequences. The expression cassette may be flanked by ϕA1122 phage DNA to allow homologous recombination of the expression cassette into the phage DNA. LuxAB may be integrated into a non-coding region of the ϕA1122 genome by homologous recombination based on a double cross over event. Recombinant ϕA1122::luxAB may be identified and isolated based on the ability of infected cultures to emit light. LuxAB integration may be verified by diagnostic agarose gel electrophoresis and PCR. The 'fitness' of the recombinant phage may be compared to the wild-type phage.

The sensitivity of the bioluminescence assay may be from about 1 CFU/mL to about 50,000 CFU/mL or about 100 CFU/mL to 1000 CFU/mL or about 1 CFU/mL to about 100 CFU/mL. In some embodiments, the sensitivity may be about 1 CFU/mL, 2 CFU/mL, 3 CFU/mL, 4 CFU/mL, 5 CFU/mL, 6 CFU/mL, 7 CFU/mL, 8 CFU/mL, 9 CFU/mL to about 10 CFU/mL.

In some embodiments, the sensitivity may be about 1 CFU/mL, about 10 CFU/mL, about 20 CFU/mL, about 30 CFU/mL, about 40 CFU/mL, about 50 CFU/mL, 60 CFU/mL, about 70 CFU/mL, about 80 CFU/mL, about 90 CFU/mL to about 100 CFU/mL. In some embodiments, the sensitivity may be from about 100 CFU/mL to about 1000 CFU/mL and may be about 100 CFU/mL, about 200 CFU/mL, about 300 CFU/mL, about 400 CFU/mL, about 500 CFU/mL, about 600 CFU/mL, about 700 CFU/mL, about 800 CFU/mL, about 900 CFU/mL, to about 1000 CFU/mL. In some embodiments, the sensitivity may include values in between the ranges listed above.

In some embodiments, the sensitivity of the assay may be about 1000 CFU/mL to about 50,000 CFU/mL, and may be about 1000 CFU/mL, about 2000 CFU/mL, about 3000 CFU/mL, about 4000 CFU/mL, about 5000 CFU/mL, about 6000 CFU/mL, about 7000 CFU/mL, about 8000 CFU/mL, about 9000 CFU/mL, about 10,000 CFU/mL, about 15,000 CFU/mL, about 20,000 CFU/mL, about 25,000 CFU/mL, about 30,000 CFU/mL, about 35,000 CFU/mL, about 40,000 CFU/mL, about 45,000 CFU/mL to about 50,000 CFU/mL.

In some embodiments of the compositions, methods, systems and/or kits of the disclosure, a reporter may comprise a nucleic acid which leads to the production of a detectable gene product. In some embodiments, the reporter may comprise nucleic acids that lead to the production of a fluorescent protein such as a green fluorescent protein (GFP), which may be detected as a green fluorescent light when exposed to UV light. In some embodiments, the reporter may comprise nucleic acids that lead to the production of a GFP, a red fluorescent protein (DsRed), or a yellow fluorescent protein or mutations and variants thereof.

In some embodiments, the reporter may comprise nucleic acids that lead to the production of an ice nucleation gene (inaZ). In some embodiments, the reporter may comprise nucleic acids that lead to the production of the beta-glucuronidase (gusA), which may be detected by colorimetric enzyme assay of cell extracts or indicator plates.

In some embodiments, the reporter may comprise nucleic acids that encode a lacZ gene, which encodes an enzyme B-galactosidase. Cells expressing B-galactosidase turn blue color when grown on a medium that contains the B-galactosidase substrate (e.g., the analog X-gal) which may be detected colorimetrically.

In some embodiments, the reporter may comprise nucleic acids that encode selectable-marker reporter which may confer an antibiotic resistant phenotype on the bacteria expressing the marker gene, e.g., a reporter may encode a chloramphenicol acetyltransferase (CAT) gene which confers resistance to the antibiotic chloramphenicol.

In some embodiments, the present disclosure relates to compositions, methods, systems and/or kits for detecting the presence of *Yersinia* bacterial cells that may not (e.g. do not) require sample processing, extensive incubation periods, or a laboratory environment. Recombinant phage cells may be mixed with a test sample suspected of comprising a *Yersinia* microorganism and subsequently analyzed for bioluminescence. A suitable aldehyde substrate (e.g. n-decanal) may be also mixed in to obtain and/or enhance bioluminescence.

The test sample suspected of comprising a *Yersinia* microorganism may be any kind of a sample including biological samples such as blood, serum, fluid from bubos, nasal fluids, respiratory tract washes, nasal swabs, throat swabs, mucous, urine, stools, or any other bodily fluids. The test sample also may be a non-biological sample such as a an air sample (e.g., air sample suspected of having aerosolized *Yersinia pestis*); an environmental sample such as a soil or a water sample; a food sample, including processed and cooked foods, raw vegetables, fruit, water, diary products, etc. Air samples may be collected by trapping a sample volume of air (from a specific location) in a tube, packet or container or by any other method known in the art to collect air samples.

Compositions, methods, systems and/or kits, according to some embodiments of the disclosure, may be configured to permit rapid detection of a microorganism such as a *Yersinia* microorganism. For example, a *Yersinia* microorganism may be detected in less than about twelve (12) hours, less than about ten (10) hours, less than about eight (8) hours, less than about six (6) hours, or less than about four (4) hours. A target microorganism may be detected in less than about three (3) hours, less than about two (2) hours, or less than about one (1) hour. A target microorganism may be detected in less than about forty minutes, less than about thirty minutes, less than about twenty minutes, less than about fifteen minutes, less than about thirteen minutes, less than about twelve minutes, less than about eleven minutes, less than about ten minutes, less than about nine minutes, less than about eight minutes, less than about seven minutes, less than about six minutes, less than about five minutes, less than about four minutes, less than about three minutes or less than about two minutes. The time required for detection may be a function of the time required for infection, and/or reporter expression and detection.

The present disclosure, in some embodiments, also relates to kits for detecting *Yersinia* microorganisms. A kit, in some embodiments, may provide components necessary and/or desired for detecting a *Yersinia* microorganism in a test sample (e.g., a biological sample obtained from a patient or animal). Non-biological samples may also be tested for the presence of *Yersinia* microorganisms to detect contamination and these include air samples, food samples including processed and cooked foods, raw vegetables, fruit, diary products, drinks, water and the like. In some embodiments *Yersinia* species that cause gastrointestinal disorders, (e.g., *Y. pseudotuberculosis* and/or *Y. enterocolitica*), may be detected for preventing food/water borne illnesses. In some embodiments, a kit may comprise compositions and/or materials for detecting *Y. pestis* in biological samples and/or from non-biological samples.

A diagnostic kit, according to some embodiments, may comprise a) a genetically engineered phage operable to infect a *Yersinia* microorganism, wherein the phage comprises a reporter gene that is detectable only after phage infection of a *Yersinia* microorganism; b) a detector substrate that forms a detectable substrate upon expression of the reporter gene; and c) one or more containers to contact (e.g., mix), the phage with a test sample that may comprise a *Yersinia* microorganism and detector substrate. Each component of the kit may be contained in a suitable container means such as a vial, tube etc. and may be comprised in suitable solvents, buffers, or reagents. Alternatively some components may be present in a dry, powdered or lyophilized form. In some embodiments, a kit may also include suitable solvents, buffers and/or reagents required to reconstitute one or more component(s) as required.

In some embodiments, a kit of the present disclosure may comprise a) a genetically engineered φA1122 phage operable to infect *Y. pestis* and comprising a luxAB reporter gene (φA1122::luxAB); b) a detector substrate for example, (e.g., an aldehyde such as n-decanal), that may react with the luxAB gene product to produce a detectable product (e.g. bioluminescent light); c) optionally a means for detecting the bioluminescent light. Each component may be packaged in suitable buffers, solutions or reagents and/or may be available as dry or lyophilized form.

In some embodiments, a kit according to the present disclosure may comprise a) a genetically engineered phage (e.g., φA1122) operable to infect *Y. pestis*, comprising a luxAB reporter gene (such as φA1122::luxAB) and a luxCDE gene; b) a means for detecting bioluminescent light. Such a kit may optionally need small amounts of a detector substrate such as an aldehyde such as n-decanal, in case the luxCDE genes do not produce sufficient substrate that may react with the luxAB gene product to produce detectable bioluminescent light. Each component may be packaged in suitable buffers, solutions or reagents and/or may be available as dry or lyophilized form.

A kit, in some embodiments, may comprise one or more standard samples comprising *Yersinia* sp., for example, *Y. pestis*, for providing a measuring standard. Phage, (e.g., recombinant phage) may be resistant to environmental extremes and/or may be stored for months or years without a significant loss in phage infectivity. Bacterial cells however, may loose their viability and/or susceptibility to phage infection after storage for long periods of time. Thus, storage periods and storage conditions for components of a kit may vary.

A container may include any vessel into which a material may be placed (e.g., a vial, test tube, flask, bottles, syringe, pipette, and/or plate other container means. The individual containers of a kit may be maintained in close confinement (e.g., for commercial sale). Suitable larger containers may include injection or blow-molded plastic containers into which the desired vials are retained. Instructions and/or safety information may be provided with a kit.

Additionally, a bioluminescence detector such as a simple photodetector may be provided. A skilled artisan, having the benefit of the present disclosure, will recognize that any photodetector known in the art may be suitably used with the compositions, methods, detection systems and/or kits of the present disclosure.

As will be understood by those skilled in the art who have the benefit of the instant disclosure, other equivalent or alternative compositions, devices, methods, systems and/or kits for detecting *Yersinia* microorganisms or other bacterial microorganisms using bacteriophages can be envisioned without departing from the description contained herein. Accordingly, the manner of carrying out the disclosure as shown and described is to be construed as illustrative only. Persons skilled in the art may make various changes in the shape, size, number, and/or arrangement of parts without departing from the scope of the instant disclosure. For example, the location of a detectable reporter gene in the phage may be changed, and/or one or more different promoters and/or other expression/regulatory control sequences from those expressly described herein may be used. In some embodiments, a *Yersinia* expression/regulatory control sequence and/or a variant of a *Yersinia* expression/regulatory control element (such as promoter), and/or a expression/regulatory control element having a synthetic or semi-synthetic component may be used in accordance to the teachings herein. In another example, the type of a detectable reporter gene in the phage may be changed.

In addition, the size of a detection method, system and/or kit may be scaled up or down to suit the needs and/or desires of a practitioner. Also, where ranges have been provided, the disclosed endpoints may be treated as exact and/or approximations as desired or demanded by the particular embodiment. In addition, it may be desirable in some embodiments to mix and match range endpoints. A composition, method system or kit may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

EXAMPLES

Some specific example embodiments of the disclosure may be illustrated by one or more of the examples provided herein. Although most of the embodiments here are described with reference to phage φA1122 and a luxAB reporter gene, it will be understood that these examples are provided for illustrative purposes only. They are not to be construed as limiting the scope or content of the disclosure in any way and any phage compatible to infect a *Yersinia* species as well as any detectable reporter gene may be used, in light of the embodiments of this disclosure.

Example 1

*Y. pestis* Strain and Phage Propagation

*Y. pestis* specific diagnostic phage φA1122 may be obtained from the CDC. The attenuated *Y. pestis* A1122 strain may be obtained from BeiResources (Bei#NR15, NIH/ATCC Biodefense and Emerging Infections Research Resources Depository). The *Y. pestis* A1122 strain is an excluded select agent strain which lacks the 75 kb low-calcium response (Lcr) virulence plasmid, and is thus irreversibly attenuated. A similar Lcr negative strain (Tjiwidej S) has been routinely used as a live vaccine in humans in Java indicating that the strain poses little to no threat to public health. Nevertheless, experiments involving *Y. pestis* A1122 may be performed under BSL2 conditions as recommended by BeiResources. *Y. pestis* A1122 may be grown on brain heart infusion (BHI) agar and liquid broth at 30° C. Clonal stocks of φA1122 phage may be prepared from single plaques. *Y. pestis* A1122 may be prepared by growing the cells in BHI media at 30° C. until an $OD_{600}$ of 0.6 is reached. The cells may be harvested by centrifugation at 4,000×g for 10 min and resuspended in BHI to an $OD_{600}$ of 2.0. Cells (100 μl) may be mixed with an equal volume of the phage preparation and incubated at room temperature for 10 min to allow pre-absorption of the phage to the bacteria. A low MOI (multiplicity of infection) may be used to select for cells that are infected by a single phage using the agar overlay method. The phage/bacteria mixture may be added to pre-warmed (47° C.) 'molten' BHI containing 0.7% agar, mixed gently, and poured over pre-warmed BHI agar plates. The plate may be left on the bench until the agar solidifies, and then incubated upside down at 30° C. overnight. Presence of plaques are indicative that phage are present.

To generate a phage stock, a distinct clonal plaque may be picked with a sterile Pasteur pipette and propagated on *Y. pestis* A1122. The phage may be amplified on progressively increasing culture volumes of exponentially growing cells in BHI media at 30° C. After each overnight growth, the cultures may be centrifuged and the supernatants passed through a 0.22 μm filter. The phage stock may be concentrated according to Carlson 2005. Sodium chloride (NaCl) may be added (at 4° C. with mixing) to the phage preparation to give a final concentration of 0.75 M and stored on ice for 60 min. The NaCl dissociates phage from the bacterial debris and improves polyethylene glycol (PEG) mediated precipitation in the subsequent steps. PEG 6000 may be added to a final concentration of 10%. After 4 h at 4° C., the phage may be collected by centrifugation at 11,000×g for 20 min at 4° C. and the resulting phage pellet may be carefully reconstituted with SMC buffer (50 mM Tris-HCl [pH7.5], 0.1 M NaCl, 8 mM $MgSO_4.7H_2O$, 0.01% gelatin supplemented with 5 mM $CaCl_2$) overnight at 4° C. The resulting phage preparation may be tittered using the agar overlay technique and stored at 4° C. until needed.

Example 2

Construction and Design of a luxAB Expression Cassette

LuxA and luxB may be PCR-amplified using the proofreading thermostable enzyme PfuUltra (Stratagene) and pQF110 (ATCC77113, contains luxAB) as template. The PCR primers may be designed to contain restriction endonuclease sites for directional cloning into the corresponding sites of pBluescriptSK$^-$ (Stratagene). The 5' primers may contain a consensus ribosome binding site (TAAGGAGGTAAAAAA(ATG)) (SEQ. ID. NO: 1) which has been shown to mediate efficient translation initiation in Gram-negative Enterobacteriaceae species. The luxA and luxB may be sequentially cloned into pBluescriptSK$^-$ (to create pluxABSK$^-$) by standard cloning methodology, and transformed into the propagating strain *E. coli* ER2738. Diagnostic restriction endonuclease analysis and agarose gel electrophoresis may be used to verify that the correct clone has been selected. The sequence of the PCR-amplified luxA and luxB genes may be verified by deoxy dye terminator sequencing.

A designed gram-negative *Yersinia* promoter (Pro1), based on conserved gram-negative promoter elements, may be used to drive luxA and luxB expression. The Pro1 promoter may contain the following conserved elements/nucleotides: (i) the −35 (TTGACA) (SEQ. ID. NO: 2) and −10 (TATAAT) (SEQ. ID. NO: 3) hexanucleotide core elements, and (ii) 5 A residues upstream of the −35 region, i.e., AAAAA (SEQ. ID. NO: 4). The designed promoter may be functional in both *E. coli*, and *Y. pestis*, and be highly expressed. A highly expressed promoter may lead to overexpression of the luxAB, high levels of bioluminescence, and potentially a high sensitivity of detection. Pro1 may be cloned upstream of luxA and luxB. To ensure efficient processing and to prevent runaway transcription (into the neighboring phage genes), the transcriptional terminator TL17 may be cloned downstream of the luxA and luxB genes (FIG. 1). The identity of the Pro1 and TL17 sequences may be verified by deoxy dye terminator sequencing.

Example 3

Generation of the ϕA1122 Targeting Vector for Homologous Recombination

The ϕA1122 phage has recently been sequenced (GenBank Accession No. AY247822 and GenBank Accession No. NC_004777), making genetic manipulation of the phage more readily achievable. The phage genome consists of 37,555 bp, with 51 predicted gene products originating from 46 distinct open reading frames. The ϕA1122 phage is very closely related to the coliphage T7 (and to a lesser extent T3) sharing a nucleotide identity of about 89%. A strategy involving direct cloning of the luxAB cassette into the ϕA1122 genome may not be pursued since the genome is large (~37 kb) making cloning difficult, and because it lacks appropriate restriction endonuclease sites. Therefore, the luxAB cassette may be integrated into the ϕA1122 phage genome by homologous recombination based on a double cross over event. The luxAB cassette may be targeted for integration at two different sites in the phage genome using two slightly different approaches: (i) the luxAB cassette may be integrated by insertion into the non-coding, intergenic region between the 'early' genes gp1.3 and pg1.5. Adding the luxAB cassette (~2 kb) into a non-coding region may not disrupt endogenous phage gene function, however, the phage genome may increase in size from ~37 kb to ~39 kb, and (ii) the ϕA1122 phage gene gp5.5 and surrounding non-coding DNA may be replaced by the luxAB cassette. Gene gp5.5 may not play an essential role in phage propagation based on the observation that mutants of the T7 gene 5.5 homolog are still functionally viable, albeit with a reduced plaque size. Replacement of the gp5.5 with the luxAB cassette, rather than insertion, may limit the increase in size of the recombinant phage genome, thereby reducing the risk of producing defective phage. Recombinant ϕA1122::luxAB generated by each approach may be compared for similarity in robustness and fitness to wild-type phage.

ϕA1122 DNA may be isolated from clarified lysates using a commercially available phage DNA isolation kit (Qiagen #12523). 500 bp fragments encompassing the 5' and 3' flanking ϕA1122 sequences may be PCR-amplified using ϕA1122 DNA as template and cloned into the pACYC184 (New England Biolabs E4152S, GenBank Accession Number X06403). pACYC184 is a multicopy *E. coli/Yersinia* shuttle vector containing multiple cloning sites, and the chloramphenicol or tetracycline resistance marker for antibiotic selection. The luxAB expression cassette may be cloned into an internal restriction site, and be flanked by the ϕA1122 DNA to create pluxABACYC184 (FIG. 2). FIG. 2 illustrates a schematic of a *Yersinia* shuttle vector and homologous recombination process based on a double crossover event. In FIG. 2, the approach of homologous recombination by replacement of the non-essential gene gp5.5 using flanking 5' (gp5.0) and 3' (gp5.7) homologous phage DNA is depicted according to some embodiments of the disclosure.

Prior to transforming the plasmids into *Y. pestis*, the plasmids may be passaged through *E. coli* SCS110 (Stratagene) in order to generate plasmid DNA free of Dam and Dcm methylation and overcome possible restriction/modification when introducing foreign DNA into *Yersinia*. The attenuated *Y. pestis* A1122 strain may be electroporated with pACYC184 (control plasmid) and pluxABACYC184 and transformants may be selected on BHI agar supplemented with antibiotic. To analyze whether the luxAB expression vector is functional and produces light in *Y. pestis*, the resulting colonies may be examined under dark field illumination. Luminescent colonies may not be obtained for the control *Y. pestis* strain harboring the empty control plasmid (pACYC184), however, luminescent colonies may be readily evident for *Y. pestis* harboring pluxABACYC184. This is an indicator that *Y. pestis* may be successfully transformed with a functioning luxAB cassette.

Example 4

Homologous Recombination

Figure 2:
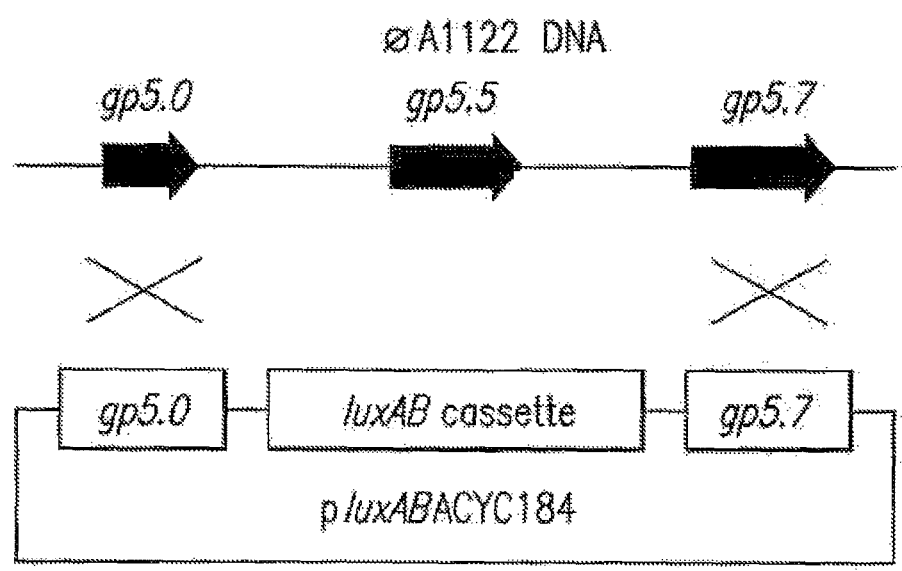
FIG. 2 illustrates a schematic of a *Yersinia* shuttle vector and homologous recombination process based on a double crossover event, according to a specific example embodiment of the disclosure.

Homologous recombination between phage and plasmid DNA based on a double crossover event may be used to integrate luxAB into the phage genome (FIG. 2). To allow for multiple rounds of phage propagation, φA1122 may be introduced into *Y. pestis* A1122 harboring pluxABACYC184 by phage infection using the agar overlay technique. Following infection and overnight growth, phage from multiple plates exhibiting confluent lysis may be eluted with 10 ml of SM buffer and filter sterilized. The titer of the phage lysates may be determined.

Example 5

Identification of Recombinant ϕa1122::luxAB Phages

ϕA1122::luxAB phage may be identified and isolated (also see Example 12 and FIGS. 3-4). Mixed phage lysates, containing predominantly wild-type ϕA1122 and a small number of ϕA1122::luxAB phages, may be used to infect *Y. pestis* A1122 using the agar overlay technique with the following modifications: (i) 24×24 cm Petri dishes may be used instead of the 'standard' 10×15 cm to allow more plaques to be screened per plate, and (ii) a high number of phage may be used for infection in combination with a short (10 h) overnight incubation to allow for the maximum number of small and nearly confluent plaques per plate. Up to 25 plates may be screened, each containing ~3,000 to 5,000 plaques per plate. The plates may be screened immediately following the addition of decanal vapor (2 μl placed on the lid of the dish) under dark field illumination. For a high frequency of recombination at least 1 to 2 plates may contain a small, but detectable light signal. Phage from the positive plates may be eluted with 20 ml of SM buffer, filter sterilized and used for re-infection of *Y. pestis* A1122 using the agar overlay technique. This screening process may be repeated until distinct individual plaques emitting a bioluminescent phenotype may be picked and isolated. High titer ϕA1122::luxAB lysates may be prepared as described in Example 1.

Example 6

Analysis and Verification of the ϕA1122::luxAB Recombinant Phage

To confirm that integration was accomplished through a double crossover event, and to verify that the plasmid DNA backbone was not integrated into ϕ1122::luxAB, phage DNA may be isolated and analyzed by diagnostic restriction agarose gel electrophoresis and PCR (also see Example 12 and FIGS. 3-4). Diagnostic restriction digests, based on the known ϕA1122 and luxAB sequences, may verify the presence of luxAB and the absence of plasmid sequence. PCR analysis may also be used to verify the presence of luxAB and absence of plasmid DNA using primers specific for luxAB (as described in Example 2) and primers specific to pACYC184, respectively. To analyze whether the luxAB integration occurred at the correct predicted site in the ϕA1122 genome, primers may be designed to span either the 5' or 3' integration junctions. Each primer set may be designed with one primer binding within the luxAB recombination cassette and one primer binding external to the recombination cassette (in the phage DNA). PCR analysis using these 'integration junction' primers may indicate that the luxAB cassette has integrated at the correct predicted site. The phage lysates may also be treated with DNase-1 (digests plasmid DNA but not 'protected' phage DNA) and subsequently used for phage infection; if DNase 1-treated cell free phage supernatants are able to transduce a bioluminescent phenotype to *Y. pestis* A1122, this may collectively indicate that intact recombinant ϕA1122::luxAB phage have been generated.

Foreign DNA may be inserted into phage without any loss of function, however, this may be dependent on phage type, the size of fragment inserted, the orientation, and the site of insertion. Therefore, the 'fitness' of the recombinant ϕA1122::luxAB phage may be compared to the wild-type ϕA1122 phage. Early exponential phase ($OD_{600}$ of 0.1) *Y. pestis* cells may be infected with the wild-type and recombinant phage at an MOI of 0.01 and incubated at 30° C. in BHI media. Following 6 h of growth, the cultures may be centrifuged, and the resulting supernatants passed through a 0.22 μm filter. The resulting phage lysates may be enumerated and analyzed using the agar overlay technique. A similar number, and a similar size of wild-type and ϕA1122::luxAB plaques may indicate that integration of luxAB into the ϕA1122 genome did not significantly impact the 'fitness' of the phage.

Example 7

Alternative Methods to Integrate luxAB into the Phage Genome

Although the ability to manipulate phage and express foreign genes is well established, integration of luxAB in a non-essential location within the phage genome may have an effect on the viability and fitness of the phage. It may also be possible that the location of luxAB, the luxAB sequence, and the addition of a strong promoter (albeit with a 3' terminator) may negatively influence phage viability. In view of this, optional and/or alternative methods may be used to integrate luxAB into the phage genome. For example, one option is to target the luxAB genes to a different non-essential (e.g., predicted) genomic location, e.g., gp19.3. In another example, a promoter with mis-matches to the consensus promoter may be used in order to reduce promoter strength (although this may also reduce luxAB expression, bioluminescence and hence, detection sensitivity). Third, the luxAB cassette without a specific promoter may be used which may rely on endogenous read-through from phage promoters. In another example, an expression cassette lacking the TL17 transcriptional terminators may be used since the terminators may prevent phage promoter read-through into genes located 3' of the luxAB genes.

Isolation of the recombinant phage may be by screening for plaques which exhibit a bioluminescent phenotype (See for example, Example 12 and FIGS. 3-4). An alternative method for the isolation of the recombinant phage may use a positive antibiotic selection pressure. For example, a streptomycin resistance gene may be included within the luxAB cassette to provide a positive selection for the isolation of 'streptomycin resistant phage'. To circumvent the concomitant use of streptomycin-tagged phage and the pathogen *Y. pestis*, an excision system (e.g., the CRE-loxP system of bacteriophage PI, the flp/frt system of *Saccharomyces cerevisiae*, the Gin system of phage Mu, Pin system of *E. coli* prophage E14, etc.) may be used to excise the streptomycin gene following isolation of the recombinant phage. Such genetic tools ensure compliance with the strict regulatory rules that are in place for the genetic manipulation of bacterial pathogens.

Example 8

Analysis of the Ability of φA1122::luxAB to Detect *Y. pestis*

The ability of φA1122::luxAB to quickly, and sensitively detect *Y. pestis* may be required for a detection system. The φA1122::luxAB may be able to detect *Y. pestis* in three hours or less, two hours and less, or one hour or less. In some embodiments, the detection may be in less than one hour, less than forty minutes, less than thirty minutes, less than twenty minutes, less than fifteen minutes, less than fourteen minutes, less than thirteen minutes, less than twelve minutes, less than eleven minutes, less than ten minutes, or less than five minutes. Phage genes may be expressed within 2-15 minutes post-infection. In some embodiments, bioluminescent light may be detected in about or less than 12 minutes of infection of an *Yersinia* microorganism by a ϕA1122::luxAB or other recombinant luxAB phage (See for Example, Example, 12 and FIG. 4). Sensitivity, dose response, and the signal response time may be analyzed. Furthermore, since ϕA1122::luxAB may be used for the detection of *Y. pestis* under diverse environmental conditions (in the field, in clinical settings etc.): (i) the phage may be stable for extended storage periods under standard conditions; (ii) the phage may remain infective over a range of pH and temperatures, and (iii) the ϕA1122::luxAB infected cultures may produce a stable light signal over a range of temperatures.

The attenuated *Y. pestis* A1122 strain (BEI#NR-15) may be for initial analysis under BSL2 conditions.

A. Signal Response Time:

The time required to generate a signal response (bioluminescence) may be assessed (also see Example 12 and FIG. 4). *Y. pestis* A1122 may be grown in BHI media at 30° C. until the mid-stages of exponential growth. Approximately $1\times10^8$ CFU/mL *Y. pestis* cells (based on Colony Forming Units after overnight growth at 30° C.) may be mixed with ϕA1122::luxAB at an MOI of 10 at 30° C. Sample processing may not be required. Bioluminescence may be measured over time using the Bio-Tek Synergy HT microplate luminometer in the presence of the substrate n-decanal (0.7% decanal, 'flash' bioluminescence). Negative controls may consist of phage or cells only. A detectable light signal from ϕA1122::luxAB-infected *Y. pestis* may be generated within 3 minutes, within 4 minutes, within 5 minutes, within 6 minutes, within 7 minutes, within 8 minutes, within 9 minutes, within 10 minutes, within 11 minutes, within 12 minutes, within 13 minutes, within 14 minutes, within 15 minutes or within 20 minutes. For example, bioluminescence may be detected from luxABM13-infected *E. coli* after only 7.5 minutes. Also, gene products of the T7 phage (closely related to the ϕA1122) may be expressed extremely quickly at 2-8 minutes post-infection at 30° C. See results in Example 12, FIG. 4 that demonstrate that ϕA1122::luxAB can effectively and rapidly detect the presence of *Y. pestis* within 12 minutes or lesser.

B. Detection of Viable Bacteria:

The ability to detect only viable and potentially infectious cells may be extremely beneficial and may be a distinct advantage over antigen and PCR tests which may detect the presence of *Y. pestis*, but yield no information as to its infectivity. To demonstrate that ϕA1122::luxAB has the ability to detect viable cells only, cells may be killed by heat treatment at 65° C. for 10 min. To ensure the cells are not viable, the cells may be plated onto BHI agar and grown at 30° C. for 48 h; no colonies are expected to form. Heat-killed cells may be mixed with ϕA1122::luxAB and assayed for bioluminescence. A bioluminescent signal is not expected since phage infection and light production may be dependent on active cell metabolism (for phage replication, and luxAB expression). The results may confirm that viable and/or potentially infectious cells may be detected by ϕA1122::luxAB.

C. Assay Sensitivity and Dose Response:

The ability to detect low concentrations of cells and to relatively quantify the number of cells present may be important characteristics of a detection methodology.

To investigate assay sensitivity and dose-dependent characteristics, a ten-fold serial dilution of cells ranging from $1\times10^8$ to $1\times10^1$ CFU/mL may be incubated with $1\times10^9$ ϕA1122::luxAB plaque forming units (PFU) as described above. Since an MOI of at least 10 may be used (MOI increases as the cells number decreases), every cell may be infected. The results in Example 12 and FIG. 4 show the detection of bioluminescence within 12 minutes upon infection of *Yersinia pestis* cells (at $1.03\times10^7$ CFU/mL), cells (n=3), with phage (50 μl of $5\times10^{10}$ PFU/mL stock), at a multiplicity of infection of approximately 10.

The results may demonstrate that as the number of cells decrease, bioluminescence decreases proportionally indicating dose-response characteristics. The lowest number of detectable cells may be determined. As the number of cells decreases, the signal response time may increase (takes longer to detect the bioluminescent signal due to fewer cells transduced and expressing luxAB).

The sensitivity of the assay may be for example, from about 500 CFU/mL to about 1,000 CFU/mL. Sensitivity of the assay may depend on the efficiency of infection, expression of the luxAB expression cassette, and the sensitivity of the luminometer. Since the human infectious aerosolized dose of *Y. pestis* are estimated to be 100-500 CFU, the sensitivity of the ϕA1122::luxAB assay may be similar to the human infectious dose.

Example 9

LuxAB Expression and Stability at Different Temperatures

LuxAB proteins may be unstable at temperatures above 30° C. Although cell growth and bioluminescence assays may be performed at 30° C., LuxAB thermostability may vary depending on the host species. For example, T7 phages may infect and replicate faster at 37° C. than 30° C. Mature T7 phage particles may be detected at 9 or 18 min after infection depending whether the incubation temperature is 30° C. or 37° C., respectively. Incubation at elevated temperatures may result in faster signal response times. LuxAB thermostability may be analyzed in *Yersinia* independently from infection. *Y. pestis* may be grown in BHI media at 30° C. Exponentially growing cells (~$1\times10^8$ CFU/mL) may be infected with ϕA1122::luxAB (~$5\times10^8$ PFU/mL). The culture may be incubated at 30° C. for 10 min to allow phage absorption to the cells, and then divided equally and incubated at various temperatures (10° C., 15° C., 20° C., 25° C., 30° C., and 35° C.). Bioluminescence may be monitored every minute for 1-50 min. Since temperature changes may also influence rates of luxAB expression (e.g., transcription and translation), changes in bioluminescence may not be strictly correlated with LuxAB stability. Crude protein lysates may then be prepared from ϕA1122::luxAB-infected *Y. pestis* and assayed for bioluminescence at different temperatures. Analysis of the crude protein lysates ensures that only preformed LuxAB may be detected and may provide an indication of LuxAB thermostability in *Y. pestis*.

Example 10

Phage Stability and Viability

An important aspect of whether the φA1122::luxAB phage may be suitable for *Y. pestis* detection may depend on the stability of lysates after long-term storage and ability of the phage to remain infective under the diverse conditions that may be encountered (e.g., outside the laboratory). Ideally, the phage may be resistant to changes in: (i) pH values; (ii) temperature, and (iii) light exposure. In general, phage are extremely stable and may survive a range of pH's (pH 4-10) and temperatures (up to 60° C.). Moreover, phage may be freeze-dried for the production of field-able detection kits. Although long-term preservation may be empirically determined for a specific phage, following lyophilization phage may be stored (e.g., at room temperature or with cooling) without a decrease in titer for years if not indefinitely.

Prior to determining phage stability, φA1122::luxAB may be concentrated and purified using polyethylene glycol (PEG). 0.75M NaCl may be added to the phage lysates and mixed continuously at 4° C. for 1 h to dissociate the phage from the bacterial debris and media components. 10% PEG 8000 may be added gradually, and the phage may be allowed to precipitate at 4° C. overnight. The precipitated phage may be collected by centrifugation (11,000×g, 15 min, 4° C.) and resuspended gently in SM buffer.

To determine the stability of φA1122::luxAB at different pH's, the pH of SM buffer may be adjusted to the following values using 1 M NaOH or 1 M HCl: pH 4, 6, 8, and 10. The purified φA1122::luxAB suspension (~1×10$^{10}$ PFU/mL) may be diluted 1/200 into pH-adjusted SM buffer and stored at ambient temperature or at 4° C. Both ambient and cold temperatures may be tested since stability at different pH's is influenced by different storage temperatures. After 24 h incubation at the designated temperatures, the number of phage may be tittered using the agar overlay technique and compared to the number of viable phage in the original starting sample. φA1122::luxAB may remain viable over a range of pH values.

Since φA1122::luxAB may be used outside of the lab after months (if not years) of storage, it may be desirable for phage to remain viable under 'standard' conditions. To determine the stability of phage preparations under different storage conditions, purified phage lysates may be stored in SM buffer in the dark at 4° C., room temperature (approx. 19° C.), and 37° C. for different durations. Phage aliquots (100 μl) may be enumerated for plaques using the agar overlay technique after 1, 2, and 3 months (and longer if possible) and compared to the original titer.

Example 11

Use of the Methods of the Disclosure to Detect Other *Yersinia* sp. and Use of Other Bacteriophage Wild-type φA1122 phage has an extraordinary ability to infect most *Y. pestis* strains, and has been used by the CDC and the WHO for the confirmed identification of *Y. pestis*. It has been shown that only two *Y. pestis* strains out of 1000's tested in the CDC collection have been identified as φA1122 resistant. A phage may infect most *Y. pestis* strains due to the lack of diversity among *Y. pestis* strains which may be due to the lack of opportunities to grow, infect, and evolve compared to other bacterial species. A potential caveat of the phage detection system, however, is the potential to infect the closely related species *Y. pseudotuberculosis*. Although temperature may be used to differentiate the species since the phage does not grow on *Y. pseudotuberculosis* at 20° C., this may not be practical, especially for use outside of the laboratory. To circumvent this one may identify (e.g., by microarray and in silico DNA analysis), and fuse a *Y. pestis* specific promoter to luxAB. Therefore, although φA1122::luxAB may infect *Y. pseudotuberculosis*, the luxAB promoter may not be expressed and light may not be produced. Alternatively, a cocktail of luxAB-*Y. pestis* phage may be used, each phage tagged with a different version of the luciferase with which emits light at a different emission spectrum. For example, the recently sequenced L-413C *Y. pestis* phage (complete genome listing GenBank Accession No: AY251033 and NC_004745), has a very broad host range within the species but in contrast to φA1122, is unable to infect *Y. pseudotuberculosis*.

Example 12

Isolation, Analysis and Detection of Recombinant φA1122::luxAB Phage

Figure 3:
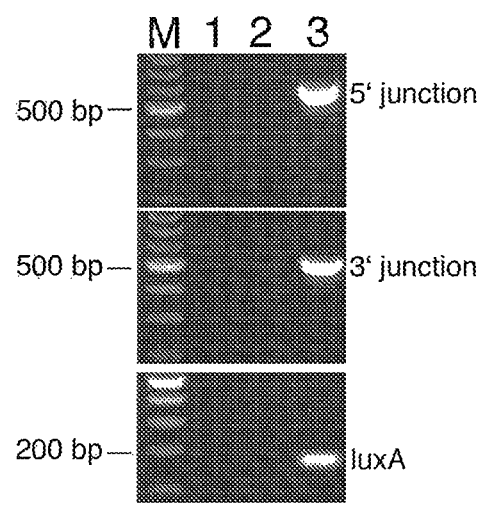
FIG. 3 shows integration of luxAB into φA1122 at the correct site in the phage genome: PCR analysis was performed in the absence of template (lane 1), with the wild-type φA1122 phage (lane 2) or with the recombinant φA1122::luxAB phage (lane 3), PCR products for the 5' junction, 3' junction, and luxA of 591, 521, and 163 bp, respectively are seen in lane 3 and not in the control lanes indicating the presence of luxA and integration of the luxAB into the φA1122 genome at the expected location, according to a specific example embodiment of the disclosure.

A. Isolation of Recombinant φA1122::luxAB Phage:

In one example, the luxAB cassette was targeted for integration into the *Yersinia* φA1122 phage genome upstream of gene 0.3 by homologous recombination. The φA1122 phage sequence at positions 897 to 903 was replaced with the luxAB cassette to generate a recombinant reporter phage with a genome size of 39,666 bp. φA1122::luxAB phage was isolated by PCR screening of serially diluted phage until an individual recombinant clone was isolated (FIG. 3).

B. Analysis of Recombinant φA1122::luxAB Phage:

To analyze whether the luxAB integration into φA1122 had occurred at the correct site in the phage genome, PCR primers were designed to span both the 5'- and 3'-integration junction sites; each primer set was designed to ensure that primer binding occurred both within and without the original integration cassette. For example, for the 5'- and 3'-integration sites, primers were designed to bind either within the recombination cassette (luxAB) or in the phage φA1122 genome at either 5' or 3' of the cassette. The predicted size of PCR products for the 5'-junction, 3'-junction, and luxA were 591, 521, and 163 bp, respectively.

PCR analysis using the primers targeting the 5' and 3' integration junction sites generated PCR products of the correct predicted size (FIG. 3), indicating that the luxAB cassette integrated at the correct loci. The gel following the PCR analysis is depicted in FIG. 3 wherein in lane 1 has the PCR product, formed with the primers described above, in the absence of template (no product seen as expected for this control); lane 2 has the PCR product, formed with the primers described above, with the wild-type φA1122 phage (no product seen as expected for this control); lane 3 has PCR product, formed with the primers described above, with the recombinant φA1122::luxAB phage (See products for the 5'-junction, 3'-junction, and luxA at the predicted sizes of 591, 521, and 163 bp in lane 3). Thus, PCR analysis shows the presence of luxA and integration of the luxAB into the φA1122 genome at the expected location. The lane "M" in the gel in FIG. 3 has the molecular weight marker that is a 100 bp marker DNA ladder.

PCR primers targeting luxA confirmed the presence of the reporter genes (FIG. 3). Since DNase 1-treated cell free phage supernatants were also able to transduce a bioluminescent phenotype to *Y. pestis* A1122, these results collectively indicated that functional φA1122::luxAB phage were generated. Titers of the recombinant phage were in the range of $10^{10}$-$10^{11}$ plaque forming units/mL (PFU/mL). This titer is comparable to titers achievable with the wild-type φA1122 and suggests that the fitness of the recombinant phage was not compromised.

C. φA1122::luxAB Detection of *Yersinia pestis*

The ability of φA1122::luxAB to transduce a bioluminescent phenotype to *Y. pestis* strain A1122 was assessed. Exponentially growing *Y. pestis* ($OD_{600}$ of approximately 0.2) were harvested and mixed with phage. For example, *Y. pestis* was grown in Luria Bertani medium at 28° C. with shaking at 225 rpm. At an OD600 of 0.185 ($1.03 \times 10^7$ CFU/mL), cells (n=3) were mixed with phage (50 μl of $5 \times 10^{10}$ PFU/mL stock, a multiplicity of infection of approximately 10), and incubated at 28° C. with shaking at 225 rpm. The ability of φA1122::luxAB to transduce bioluminescence (Relative Light Units, RLUs) was monitored over time using a Synergy II multiplate detection reader, following the addition of a luciferase substrate such as 2% n-decanal (as depicted in FIG. 4).

Figure 4:
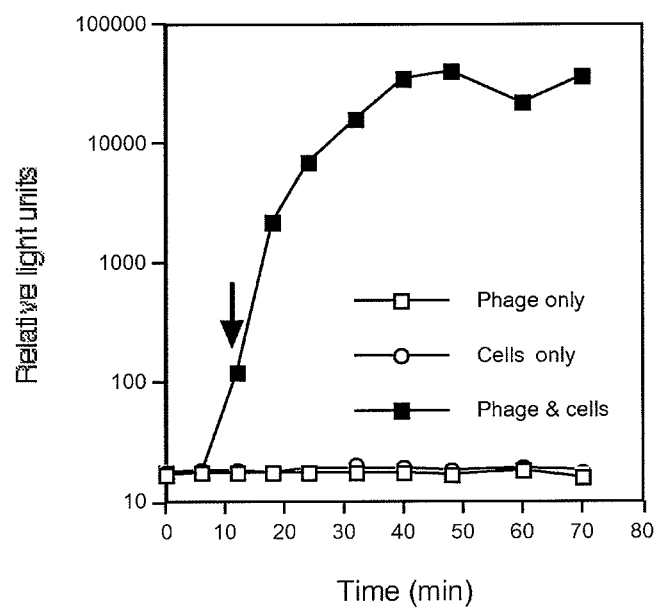
FIG. 4 illustrates detection of *Y. pestis* by φA1122::luxAB measured as bioluminescence (RLU) over time following the addition of 2% n-decanal, according to a specific example embodiment of the disclosure.

A steady increase in bioluminescence was detected from *Y. pestis* phage-infected cells (FIG. 4). A detectable light signal above background (phage alone or cells alone) was evident within 12 minutes after phage infection. The results indicate that: (i) the φA1122::luxAB phage were able to infect and transduce a bioluminescent phenotype to *Y. pestis*; (ii) the luxAB genes were functional in *Y. pestis* and produced a steady detectable bioluminescent signal, and (iii) a rapid signal response time at about 12 minutes after phage infection (FIG. 4, See arrow). Controls consisted of cells or phage alone. Numbers are the average±SD of 3 infections (FIG. 4).

These equivalents and alternatives along with obvious changes and modifications are intended to be included within the scope of the present disclosure. Moreover, one of ordinary skill in the art will appreciate that no embodiment, use, and/or advantage is intended to universally control or exclude other embodiments, uses, and/or advantages. Expressions of certainty (e.g., "will," "are," and "cannot") may refer to one or a few example embodiments without necessarily referring to all embodiments of the disclosure. Accordingly, the foregoing disclosure is intended to be illustrative, but not limiting, of the scope of the disclosure.

REFERENCES

The following references, to the extent that they provide exemplary procedural or other details supplementary to those set forth herein, are specifically incorporated herein by reference.

Abremski, et al., 1986, *J Biol Chem* 261:391-6.
Bossi, et al., 2006, *Cell Mol Life Sci* 63:2196-212.
Calendar, et al., 2005, Oxford University Press.
Carlson, 2005, CRC Press, Boca Raton.
Choi, K. H., et al., 2008, *Appl Environ Microbiol* 74:1064-75.
Conchas, R. F., et al., 1990, *Gene* 87:133-7.
D'Aoust, J. Y., et al., 1988, *J Dairy Sci* 71:3230-6.
Dennis, D. T., et al., 1999, *Plague Manual: Epidemiology, Distribution, Surveillance, and Control.*
Escher, A., et al., 1989, *Proc Natl Acad Sci USA*, 86:6528-32.
Garcia, E., et al., 2003, *J Bacteriol*, 185:5248-62
Garcia, E., et al., 2008, *Virology*, 372:85-96.
Lin, L. Y., et al., 2004, *Biochemistry*, 43:3183-94.
Liu, Q., et al., 1993, *Proc Natl Acad Sci USA*, 90:1761-5.
Loessner, M. J., et al., 1996, *Appl Environ Microbiol.*, 62:1133-40
Mackey, B. M., et al., 1994, *J Appl Bacteriol.*, 77:149-54.
Meyer, K. F. 1974, *Plague immunization. Journal of Infectious Diseases* 129:S13-S18.
Sambrook, J., et al., 1989, Cold Spring Harbor Press, New York.
Schofield, D. A., et al., 2001, *J Bacteriol.*, 183:6947-50.
Schofield, D. A., et al., 2002, *Curr Microbiol.*, 44:425-30.
Schofield, D. A., et al., 2002, *FEMS Microbiol Lett.*, 215:237-42.
Schofield, D. A., et al., 2003, *Appl Environ Microbiol.*, 69:3385-92.
Sternberg, N., et al., 1981, *J Mol Biol.*, 150:467-86.
Studier, F. W. 1981. *J Mol Biol.*, 153:493-502.
Westwater, C., et al., 2005, CRC Press, Boca Raton.
Wright, J. J., et al., 1992, *Embo J* 11:1957-64.
Young, R. 1992, *Microbiol Rev.*, 56:430-81.
Zierdt, C. H. 1988, *Appl Environ Microbiol.*, 54:2590.

What is claimed is:

1. A phage operable to infect a *Yersinia* microorganism comprising a detectable reporter configured and arranged to be expressed in the *Yersinia* microorganism upon infection of the microorganism by the phage, the detectable reporter comprising a nucleic acid encoding a luxAB gene inserted into the nucleic acid by homologous recombination, wherein the expression of the luxAB gene is detected as bioluminescent light.

2. The phage of claim 1, wherein the detectable reporter further comprises at least one expression control element operably linked to the luxAB gene.

3. The phage of claim 1, wherein the phage comprises a phage selected from the group consisting of serovar 1, serovar 2, serovar 3, and serovar 4.

4. The phage of claim 1, wherein the phage is a lytic phage.

5. The phage of claim 4, wherein the phage comprises a φA1122.

6. The phage of claim 1, wherein the phage is a temperate phage.

7. The phage of claim 6, wherein the phage comprises a L-413C.

8. The phage of claim 1, wherein the *Yersinia* microorganism is *Yersinia pestis*.

9. The phage of claim 1, wherein the *Yersinia* microorganism is selected from the group consisting of *Yersinia enterocolitica*, *Yersinia pseudotuberculosis*, and combinations thereof.

10. The phage of claim 2, wherein the expression control element comprises one or more *Yersinia* expression control elements.

11. The phage of claim 10, wherein the one or more *Yersinia* expression control elements are selected from the group consisting of transcriptional control elements, translational control elements and combinations thereof.

* * * * *